United States Patent [19]

Devos et al.

[11] Patent Number: 4,849,023

[45] Date of Patent: Jul. 18, 1989

[54] PROCESS FOR THE PREPARATION OF A PRODUCT WITH A HIGH CONTENT OF MALTITOL AND USES OF THIS PRODUCT

[75] Inventors: Francis Devos, Hazebrouck; Pierre-Antoine Gouy, Lambersart, both of France

[73] Assignee: Roquette Freres, Lestrem, France

[21] Appl. No.: 143,273

[22] Filed: Jan. 6, 1988

[30] Foreign Application Priority Data

Dec. 20, 1984 [FR] France ................ 84 19601

Related U.S. Application Data

[63] Continuation of Ser. No. 810,247, Dec. 18, 1985, abandoned.

[51] Int. Cl.⁴ .................. C13K 1/08; C13K 13/00; C07C 27/00
[52] U.S. Cl. .......................... 127/40; 127/38; 127/46.1; 127/46.2; 127/46.3; 127/58; 127/36; 568/872; 568/863
[58] Field of Search ............... 127/36, 38, 40, 46.2, 127/46.3, 58, 46.1; 568/872, 863

[56] References Cited

U.S. PATENT DOCUMENTS 3,708,396 1/1973 Mitsuhashi et al. ............... 568/863
4,346,116 8/1982 Verwaerde et al. ............... 426/548
4,408,041 10/1983 Hirao et al. ...................... 426/660
4,487,198 12/1984 Miyake et al. .................... 127/46.3

FOREIGN PATENT DOCUMENTS 0072080 2/1983 European Pat. Off. .
2826120 12/1979 Fed. Rep. of Germany ...... 568/872
2000580 9/1969 France .

OTHER PUBLICATIONS

*Hydrolysis of the Amylopectins,* vol. 25, Jan. 1948, "Hydrolysis of the Amylopectine from Various Starches with Beta Amylase", by J. E. Hodge et al., pp. 19–30.
*Methods in Carbohydrate Chemistry,* Whistler, vol. I, 1962, "Purification of Commercial Maltose", by M. L. Wolfrom and A. Thompson, pp. 334–339.

Primary Examiner—Patrick P. Garvin
Assistant Examiner—Chung K. Pak
Attorney, Agent, or Firm—Larson and Taylor

[57] ABSTRACT

Process for the preparation of a product with a high content of maltitol, characterized by the following steps:
 catalytic hydrogenation of a maltose syrup,
 chromatographic fractionation of the maltitol syrup formed during the hydrogenation step,
 adjustment to the desired dry matter of at least the fraction enriched in maltitol.

1 Claim, 2 Drawing Sheets

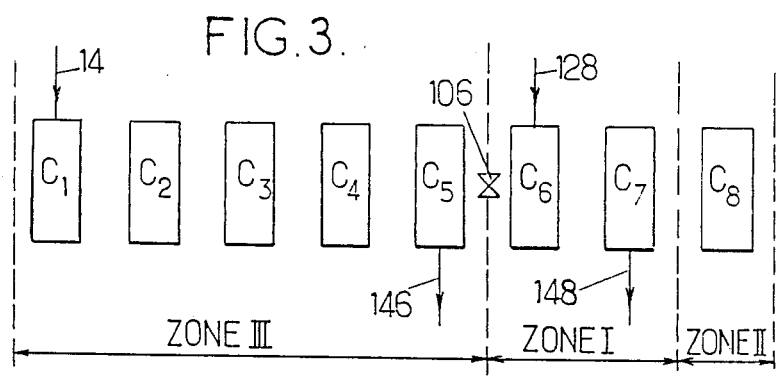
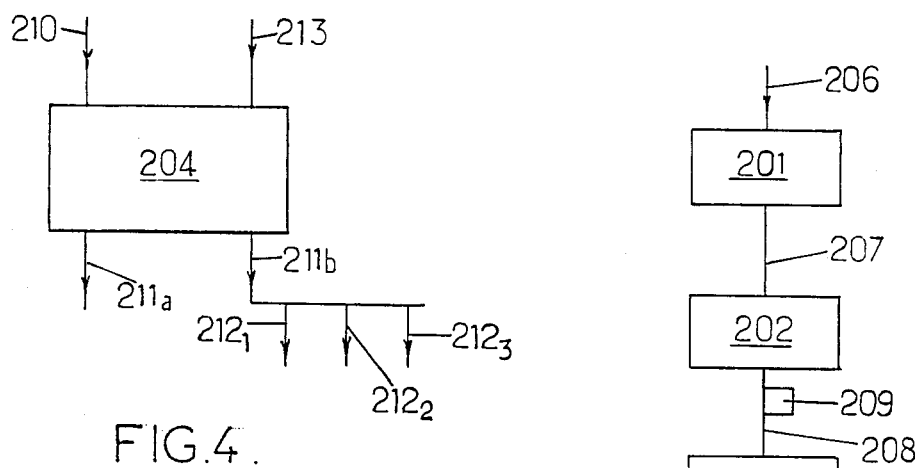
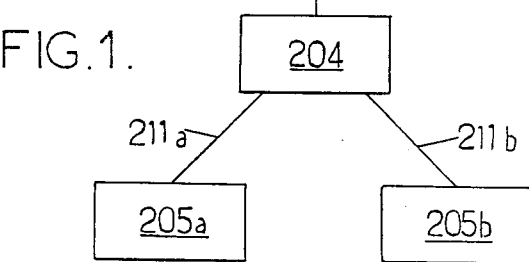

PROCESS FOR THE PREPARATION OF A PRODUCT WITH A HIGH CONTENT OF MALTITOL AND USES OF THIS PRODUCT

This application is a continuation of application Ser. No. 810,247 filed 12/18/85, now abandoned.

The invention relates to a novel process for the manufacture of a product with a high content of maltitol.

It relates also to the product obtained by this process and the uses of this product.

It is recalled that maltitol or (α-D-glucopyranosyl)-4-D-sorbitol or again (4-O-α-D-glucopyranosyl)-D-glucitol constitutes the result of the hydrogenation of maltose.

Various processes are known enabling maltose-rich syrups to be obtained.

Among these processes, may be cited:

that described by HODGE et coll. in "Cereal Chemistry" no. 25, pages 19-30, January 1948, and which comprises a precipitation step of the limiting dextrins by alcoholic solutions, that described by WOLFROM and THOMPSON in "Methods in carbohydrate chemistry", 1962, pages 334-335, and which comprises a repeated crystallization step of the maltose octaacetate followed by the crystallization of the maltose.

that described in U.S. Pat. No. 4,294,623 of MEIJA SEIKA granted 10.13.81 and which comprises a step of adsorption on charcoal of the dextrins, that described in FR Pat. No. 2,510,581 of HAYASHIBARA filed 08.03.82 and which comprises a step of chromatography on zeolites or cationic or anionic resins, that described in U.S. Pat. No. 4,429,122 of U.O.P. and which comprises an ultrafiltration step of the maltose syrups, and that which is described in FR Pat. No. 2,012,831 of HAYASHIBARA filed 03.27.70 and which comprises the combined use of several different enzymes, namely an α-amylase, a β-amylase and an isoamylase pullulanase.

The latter technique presents, with respect to the preceding ones, numerous advantages.

It suffers nonetheless from certain drawbacks, among which are particularly:

that residing in the fact that the liquefaction must be carried out at very low values of DE, an inopportune retrogradation of the amylose at these low hydrolysis ratios spoiling the following operations of saccharification and purification.

that residing in the fact that the saccharifications must be carried out at contents of dry matter which are very low, of the order of 20 g/l, to obtain a maximum efficiency of hydrolysis of the enzymes.

It follows that none of these techniques enable the obtaining easily and economically of syrups with a high content of maltose suitable to provide by hydrogenation syrups with a high content of maltitol.

In addition, these techniques do not permit the obtaining easily of products of sufficient purity.

In particular, they show especially a content of products of DP≧4 greater than 1% by weight with respect to the dry matter.

Now it happens that Applicants have developed a novel process which is extremely effective and suitable to provide easily a product with a high content of maltitol.

This process provides simultaneously a product rich in maltotriitol.

In this new process it is possible to utilize maltose syrups having an intermediate richness (containing from 50 to about 80% maltose) which are obtained easily and economically.

This novel process rests essentially on the discovery of the fact that any maltose syrup, containing more than 50% by weight of maltose with respect to the dry matter, is suitable to provide, after hydrogenation and by chromatographic fractionation, particularly a syrup rich in maltitol practically free of hydrogenated polysaccharides of DP equal to or greater than 4 and containing very little sorbitol and maltitriitol.

It follows that the process according to the invention is characterized by the fact that a syrup containing at least 50% by weight of maltose, is subjected successively:

to a catalytic hydrogenation and
to a chromatographic fractionation.

Subsequently, by concentration or by dilution at least the maltitol rich fractions are brought to the desired dry matter content.

BRIEF DESCRIPTION OF THE DRAWINGS

FIG. 1 is a diagrammatic flow sheet illustrating the installation for carrying out the process in accordance with the invention;

FIG. 3 is a diagrammatic representation of the installation of FIG. 2 showing the desorption zone, the adsorption zone and the enrichment and separation zone;

FIG. 4 is a diagrammatic flow sheet illustrating a modification of the installation shown in FIG. 1.

Figure 2:
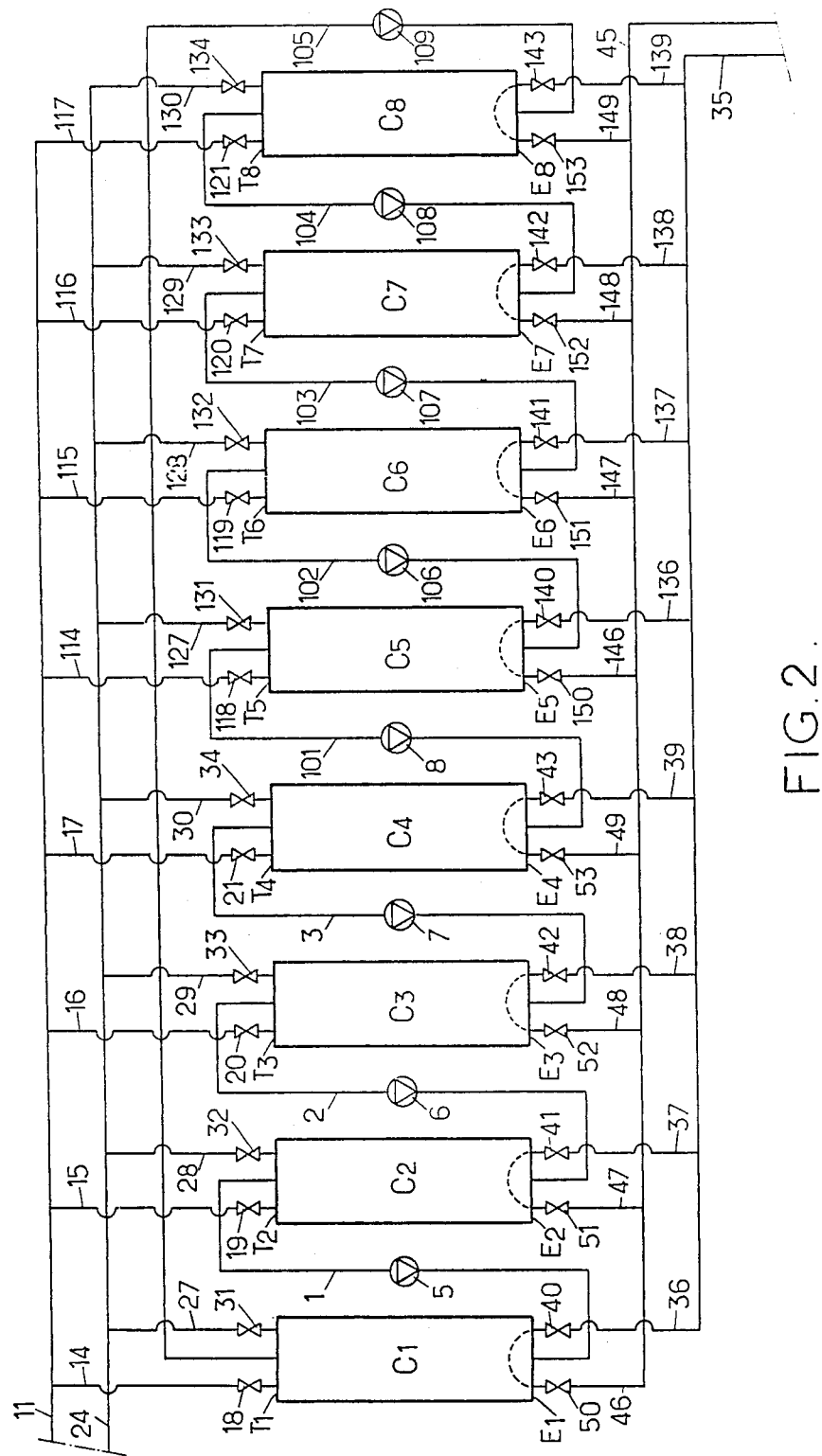
FIG. 2 is a diagrammatic view of an installation suitable for carrying out a chromatographic fractionation step in the process in accordance with the invention.

More precisely, the process according to the invention can be employed by means of the installation shown diagrammatically in FIG. 1 and which comprises:

a vessel 201 within which liquefaction of the starch is performed, a vessel 202 within which the saccharification of the starch is performed, a vessel 203 within which the catalytic hydrogenation is performed, a vessel 204 for chromatographic separation, one or several vessels 205a, 205b . . . , enabling the concentration alternately or each continuously the various fractions emerging from the chromatography to the desired dry matter contents.

The vessel 201 is supplied through a pipe 206 with starch or fecula milk supplemented acid in the case of acidic liquefaction or with an α-amylase in the case of enzymatic liquefaction, under the conditions of dry matter content, of pH, of enzyme ratio and of calcium known by the man skilled in the art, to obtain a DE (dextrose-equivalent) equal to or higher than 2.

The vessel 202 is supplied through a pipe 207 with liquefied starch syrup emerging from the vessel 201; before its entry into the vessel 202, there is added to the syrup emerging from the vessel 201, a malt amylase and as the case may require, an enzyme hydrolizing the α 1-6 linkages; procedure continues under the conditions and in the manner known in themselves, so that there is obtained a richness of maltose of 50% at least at the outlet of the vessel 202.

The vessel 203 is supplied from the vessel 202 and through a pipe 208 with saccharified syrup, then filtered and demineralized in a device 209 placed in the pipe 208.

In the vessel 203 catalytic hydrogenation follows of the maltose syrup under conditions well known to the man skilled in the art, particularly with ruthenium or Raney nickel catalysts.

Preferably, the hydrogenation step is carried out with a Raney nickel catalyst, at a hydrogen pressure higher than 20 g/cm$^2$, preferably comprised between 40 and 70 kg/cm$^2$ and at a temperature of about 100° to 150° C. The hydrogenation is continued until the content in reducing sugars of the hydrogenated syrups is less than 2%, preferably less than 1% and still more preferably less than 0.5% (the content in reducing sugars being defined in weight equivalent of dextrose with respect to the dry matter.

The vessel 204 is supplied through a pipe 210 with hydrogenated syrup emerging from the vessel 203, this syrup being purified and concentrated in devices not shown on FIG. 1.

There follows in the vessel 204 a chromatographic fractionation.

Through the pipes 211a, 211b... are led the fractions emerging from the vessel 204.

The chromatographic fractionation step can be done in manner known in itself, discontinuously or continuously (simulated mobile bed), on adsorbents of the highly acid cationic resin type, charged with alkaline or alkaline-earth ions or again of the zeolite type charged with ammonium, sodium, potassium, calcium, barium, strontium, etc. ion....

Examples of such processes of chromatographic separation are given in U.S. Pat. No. 3,044,904, U.S. Pat. No. 3,416,961, U.S. Pat. No. 3,692,582, FR 2,391 754, FR 2,099,336, U.S. Pat. No. 2,985,589, U.S. Pat. No. 4,024,331, U.S. Pat. No. 4,226,977, U.S. Pat. No. 4,293,346, U.S. Pat. No. 4,157,267, U.S. Pat. No. 4,182,633, U.S. Pat. No. 4,332,633, U.S. Pat. No. 4,405,445, U.S. Pat. No. 4,412,866, and U.S. Pat. No. 4,422,881.

According to a preferred embodiment, the separation step is carried out by employing the process and the apparatus described in U.S. Pat. No. 4,422,881 and its corresponding French Pat. No. 79 10563.

Whatever the chromatographic separation process used, recourse is had, preferably, as absorbent, to a strong cationic resin placed in the calcium form and having a ratio and divinylbenzene of about 4 to 10%.

The efficiency of the chromatographic enables to exlude practically in totality from the maltitol fraction the hydrogenated products having a DP (degree of polymerization) higher than or equal to 4 even if the syrups subjected to fractionation contain important quantities of those sugars for instance comprised between 5 and 40%.

Consequently it is possible to have recourse to starch hydrolizates whose richness in maltose is only 50%.

Consequently, it is possible to employ starch milks with high dry matter contents, in any case comprised between 25% and 45% and close to 40% like those which it is customary to employ in glucose-dextrose plants.

Thus, the volumes to be treated are indeed less than in prior processes, the energy necessary for the evaporation of the water is found to be much reduced, the liquefaction of the starch can be done at a DE higher than 2, compatible with an absence of retrogradation of the starch, the use of expensive enzymes like isoamylase or pullulanase can be avoided, the high osmotic pressure occasioned by the high concentration of the syrups also shielding these from any microbial contamination.

According to the invention, the liquefaction may be done by the acid or by the enzymatic route.

The parameters of the enzymatic saccharification:
kind of enzyme ($\beta$-amylase of vegetal or bacterial origin possibly in combination with a debranching enzyme
amount of enzyme
temperature of an amylolysis and
duration of amylolysis
are generally selected in such a manner that the content in maltose of the syrups as obtained is 50 to 80% and preferably 60 to 80% on dry matter.

In the process according to the invention, the parameters of the chromatographic separation step are selected so that there is obtained, besides a syrup enriched in maltotriitol and a syrup composed of hydrogenated products of high molecular weight, a maltitol syrup having a richness at least equal to 87% by weight of maltitol, preferably from 87 to 97.5% and more preferably still, from 87 to 95.5% of maltitol, containing less than 1% of maltotetraitol and hydrogenated products of higher molecular weight.

As regards to the selection of the parameters of the chromatographic separation step, i.e; in particular
the elution rate
the supply rate with hydrogenated syrup
the extraction rate of the fraction rich in maltitol
the composition of the desorption, adsorption and enrichment zones
it is illustrated in the examples, Preferably, the above-said maltitol syrup contains a proportion of sorbitol less than 5%, preferably less than 3% and, still more preferably, less than 2%.

Its content of maltotriitol is generally comprised between 2.5 and 13% by weight.

The product obtained according to the invention may be presented in the form of a liquid product, generally marketed with a dry matter higher than 65%, or in the form of a non-hygroscopic dry powder, obtained from said liquid product, for example by solidification and drying of very concentrated solutions.

This product in its adapted physical form may be used as a sweetening or moistening agent in "edible products", by which expression is meant products intended for oral absorption, such as various food substances like confectionery, pastries, creams, drinks and jams, as well as pharmaceutical, dietetic, cosmetic or hygenic products, such as for example elixirs and syrups for combatting coughs, tablets or pills and opaque or transparent toothpastes.

It has, in fact, several advantages which lend it very particularly to these uses.

The innocuousness of its principal constituent, maltitol, is fully demonstrated and recognized.

Maltitol is a substance metabolized at the level of the digestive tract. Thus it has been demonstrated in the animal that the complex maltase-glucoamylase ("New approach to the metabolism of hydrogenated starch hydrolysate". In the press. ROSIERS C., VERWAERDE F., DUPAS H., BOUQUELET S., Laboratoire de chimie biologique, Université des Sciences et Techniques de LILLE I and Laboratory associated with the C.N.R.S. no. 217-Director: J. MONTREUIL-59655

VILLENEUVE D'ASCQ CEDEX, France), present particularly at the level of the duodenum, hydrolyses the glucose α-1,4-sorbitol linkage, thus liberating one molecule of sorbitol whose absorption is effected by a passive route, and one molecule of glucose whose passage through the intestinal mucous membrane occurs by active transfer with the intervention of a sodium and potassium dependent membranal adenosine-triphosphatase ("Sugars in Nutrition" SIPPLE H. L., MAKINEN K. N., Acad. Press 1974).

The studies undertaken in man have confirmed the results obtained in the animal. The metabolism of the maltitol liberates glucose and sorbitol, two molecules whose metabolic fate is well known ("Digestion of maltitol in Man, Rat and Rabbit" ZUNFT H. J., SCHULZE J., GARTNER H., GRUTTE F. K.; Ann. Nutr. Metab. 27 (1983) p. 470-476).

The digestion of this product is manifested by a rise in the glycemia and the insulinemia. It appears however that the rise in the glycemia is more spread out over time than that observed after the adsorption of an equivalent charge of glucose or of saccharose ("The metabolic fate of hydrogenated glucose syrups" KEARSLEY M. W., BIRCH G. C., LIAN-LOH R. H. P., "Die Stärke" 34 (1982) Nr. 8, p. 279-283). Urinary and fecal assays indicate that a small amount of maltitol may escape intestinal hydrolysis. Nonetheless, according to different authors, the caloric use of maltitol is situated between 90 and 99% of the ingested dose ("Metabolism and caloric utilization of orally administered Maltitol 14C in rat, dog and man", RENNHARD H. H., BIANCHINE J. R.; Journal Agric. Food Chem., Vol. 24 no. 2, 1976, p. 287-291). Consequently it is possible to forecast that the digestion tolerance of the product obtained according to the invention will be linked with that of glucose and of sorbitol and that it will hence be excellent, both in the child and in the adult.

The sweetening power of the product obtained according to the invention is on the other hand high, close to that of saccharose.

Its moistening power and its moisture-retaining properties are very advantageous in certain confectionery products as well as in dentifrices and jellies, It is moreover stable to heat, not causing reactions of caramelization or of browning by heating in the presence of proteins.

Through its very special composition, characterized by a very high content of maltitol and especially by an extremely low content of hydrogenated oligosaccharides of DP higher than or equal to 4, it shows, in addition, an extremely low cariogenicity and a relatively high and constant viscosity.

It can also be used in fields such as textile industries, foundry works, paper-making, by reason particularly of its moistening and plasticising power; it can also be used as a chemical or synthesis intermediate, uses in which its high richness in maltitol and its very low content of polyols of DP higher than or equal to 4 can show determining advantages, from the point of view for example of the viscosity and the homogeneity of the molecular mass and properties of the finished products obtained; thus it can be used in the manufacture of polyurethanes, in the preparation of polyesters or polyethers, and in the preparation of fatty acid esters.

Through its very low content of hydrogenated oligosaccharides of DP higher than or equal to 4, the product obtained according to the invention lends itself very easily to the manufacture of crystalline maltitol, due to the spontaneous formation and in large amount of maltitol crystals.

This particular aptitude is due to the original composition of the product according to the invention.

The invention will be still better understood by means of the examples which follow and of FIGS. 2 to 4 which relate thereto; said examples relate to advantageous embodiments of the invention but which in no way limit the scope thereof.

The examples are divided into two groups.

The first group encompasses the two first examples; the latter relate to the novel process of manufacturing the maltitol rich product, according to the invention.

The second group encompasses Examples 3 to 6; the latter relate to uses of the product obtained according to the invention.

EXAMPLE 1—PROCESS FOR THE PREPARATION ACCORDING TO THE INVENTION OF A SYRUP WITH A HIGH MALTITOL CONTENT FROM A CORN STARCH MILK (a) Preparation of a maltose rich syrup A corn starch milk with 37% of dry matter is subjected to conventional enzymatic liquefaction by means of thermoresistant α-amylase.

Thus $0.6°/_{oo}$ of the thermoresistant enzyme of the NOVO Company known under the name "THERMAMYL" is added and the whole is kept at 107° C. for 6 minutes. A solution with 37% of dry matter having a DE of 7.5 is thus obtained.

There are then added conjointly β-amylase malt (namely $0.5°/_{oo}$ of that known under the name "MEZYME" of the FINNSUGAR Company) and pullulanase ($2°/_{oo}$ of that known under the name "PULLUZYME 750L" of A.B.M.), the pH being 5.7 and the temperature 57° C.

After having maintained the conjugate action of the two enzymes for 48 hours, a syrup is obtained whose composition was as follows:

| | |
|---|---|
| dextrose | 1.8% by weight |
| maltose | 74.9% by weight |
| maltotriose | 15.9% by weight |
| Products of DP 4 to DP 10 | 4.8% by weight |
| Products of DP > 10 | 2.6% by weight. |

(b) Preparation of a maltitol rich syrup

After purification on active charcoal and demineralization, catalytic hydrogenation followed of the maltose syrup (dry matter content 45% by weight) under conventional conditions, at a temperature of 125° C. and at a hydrogen pressure of 55 kg/cm².

As catalyst, Raney nickel was used.

The hydrogenated syrup had the following composition after purification on ion exchange resins:

| | |
|---|---|
| sorbitol | 3.2% by weight |
| maltitol | 73.1% by weight |
| maltotriitol | 14.8% by weight |
| products of DP 4 to DP 10 | 5.9% by weight |
| hydrogenated polysaccharides of DP > 10 | 3.0% by weight. |

(c) Chromatographic fractionation step

The maltitol rich syrup obtained in the preceding step is concentrated to 52.5% of dry matter.

It is then led onto a chromatographic separation installation whose details of construction and operation are those described in U.S. Pat. No. 4,422,881 and in the corresponding French Pat. No. 79 10563, these details being only taken up again here to the extent that comprehension of the description requires it.

This installation comprises, as shown in FIG. 2 of the American patent (taken up again here as FIG. 2, for a detailed explanation of which reference will be made to the American patent), eight columns or stages $C_1$ to $C_8$ of 200 liters each, lined with adsorbent of the strong cationic resin type in the calcium form and of fine granulometry (0.2 to 0.4 millimeters).

By calibration of the electrovalves, a two stage desorption zone I is established, a one stage adsorption zone II and an enrichment and separation zone III for the hydrogenated limiting dextrins and the maltotriitol of five stages.

This arrangement is illustrated by FIG. 3 which is a diagramatic representation of the installation according to FIG. 2 and in which there is shown only:
- columns $C_1$ to $C_8$,
- the closure device, in the event the electrovalve 106,
- the pipes for supplying maltitol syrup to be fractionated and water, shown respectively at 14 and 128, and
- the pipes for the extraction of maltitol-enriched syrup, on the one hand, and limiting dextrins and maltotriitol, on the other hand, shown respectively at 148 and 146.

The closure device 106 maintains in the configuration adopted, total fluid-tightness between, on the one hand, the zone III, which is an enrichment zone at the end of which are hence recovered successively the strongly adsorbed sorbitol reliquate, the hydrogenated limiting dextrins, then the fraction enriched in maltotriitol, on the other hand, the maltitol desorption zone I, at the head of which zone is introduced the desorption water.

This closure device ensures the direction of passage of the liquid phase over the selective adsorbent and avoids especially contamination of the enriched maltitol by traces of hydrogenated limiting dextrins with high molecular weight, whose speed of migration within the resin is largely superior to that of the maltitol.

A timing device adjusted to 23'30" ensures for the flow rates indicated below a sufficient supply of water to effect the desorption of the whole of the maltitol at the first stage of the desorption zone I, and a supply of a volume of hydrogenated starch hydrolyzate rich in maltitol compatible with the volume of adsorbent and its adsorption capacity, so as to obtain an extraction ratio of maltitol at least equal to 90% of the maltitol present in the hydrogenated hydrolyzate and this at a richness at least equal to 87% in true maltitol. The syrup obtained has a content less than 0.5 % of products of DP greater than or equal to 4.

The above-said levels of extraction and purity were kept constant by adjusting the flow rate of the extraction pump (not shown) of the adsorbed maltitol. The outflow of the "hydrogenated limiting dextrins" and "enriched maltotriitol" was effected at atmospheric pressure and its constant flow rate results from the difference between the supply flow rate and the extraction flow rate.

The hydrogenated starch hydrolyzate rich in maltitol which is introduced into the installation at the head of the enrichment stage III has, as indicated above, a dry matter content of 52.3%. The temperature within the separation column was maintained at about 90° C.

FIG. 4 shows diagrammatically at 204 the installation of FIG. 2 (the same reference numerals denoting the same elements for the common parts as in FIG. 1). The chromatography installation includes a pipe 211b through which the excess water containing an important fraction of sorbitol and the hydrogenated limiting dextrins fraction with molecular weight higher than or equal to DP 4 are removed; these extracts are of low dry matter content and exit through pipes $212_1$ and $212_2$.

The supply of water is effected through a pipe 213.

The arrows borne on the pipes indicate the direction of flow.

The whole operates as follows:

the hydrogenated starch hydrolyzate which has to be subjected to chromatographic fractionation is led through the pipe 210 at a flow rate of 96.9 liters/hour and has a dry matter content of 52.3%, the water is introduced through the pipe 213, with a flow rate of 393 liters/hour, the enriched maltitol free from hydrogenated limiting dextrins is recovered through the pipe 211a with a flow rate of 152 liters/hour, its average content of dry matter being 28.6%, the total amount of liquids extracted from the installation is extracted with a total flow rate of 337.9 liters/hour, being composed successively:

of an excess water fraction, extracted through the pipe $212_1$, containing, at low concentration and high purity, sorbitol and a fraction at low concentration and of high richness in hydrogenated limiting dextrins with DP greater than or equal to 4 extracted through the pipe $212_2$, the whole representing an equivalent of 266 liters/hour, the dry matter content being 2.4%; these fractions corresponded to the 18.5 first minutes of the cycle, of a fraction of an enriched maltotriitol, of an equivalent of 71.9 liters/hour led through a pipe $212_3$ to a purification installation (not shown) the content of dry matter of this fraction being 10%; this fraction corresponds to the five last minutes of the cycle.

The analyses of the enriched maltitol effluents on the one hand, of sorbitol, of hydrogenated limiting dextrins and of enriched maltotriitol on the other hand are, by way of indication, given respectively in Table I for maltitol, and in Table II for the others.

TABLE I

| | ENRICHED MALTITOL Effluent | | | | | |
|---|---|---|---|---|---|---|
| Time | Dry Matter in % | Constituents of DP > 4 | DP 4 | DP 3 | Maltitol | Hexitols |
| 0 | 48 | 0 | 0.7 | 12.6 | 86.4 | 0.3 |
| 2 | 47 | 0 | 0.4 | 10.3 | 89.0 | 0.3 |
| 4 | 46 | 0 | 0.3 | 7.2 | 92.1 | 0.4 |
| 6 | 44.5 | 0 | 0.1 | 5.9 | 93.6 | 0.4 |
| 8 | 44 | 0 | 0 | 4.5 | 94.5 | 1.0 |
| 10 | 39 | 0 | 0 | 3.7 | 95.2 | 1.1 |
| 12 | 35 | 0 | 0 | 3.4 | 95.4 | 1.2 |
| 14 | 30 | 0 | 0 | 3.2 | 95.2 | 1.6 |
| 16 | 24 | 0 | 0 | 3.0 | 95.2 | 1.8 |
| 18 | 19 | 0 | 0 | 3.0 | 95.0 | 2.0 |
| 20 | 14 | 0 | 0 | 2.7 | 94.8 | 2.5 |
| 22 | 9.5 | 0 | 0 | 2.7 | 94.3 | 3.0 |
| 23'30" | — | 0 | 0 | | — | |

TABLE I-continued

| | ENRICHED MALTITOL Effluent | | | | |
|---|---|---|---|---|---|
| Time | Dry Matter in % | Constituents of DP > 4 | DP 4 | DP 3 | Maltitol | Hexitols |
| Average | | 0 | 0.2 | 5.9 | 93.3 | 0.6 |

From examination of Table I, it appears that the maltitol was extracted for 23'30", at an average purity of 93.3% of maltitol and with an average dry matter content of 28.5%.

The true hexitol content was 0.6%, that of the hydrogenated products of DP 4, was 0.2%.

All the higher hydrogenated limiting dextrins were removed from this fraction by means of this fractionation technology.

TABLE II

| | ENRICHED MALTOTRIITOL Effluent | | | | | |
|---|---|---|---|---|---|---|
| Time | Dry Matter in % | Constituents of DP > 5 | DP 5 | DP 4 | DP 3 | DP 2 | Hexitols |
| 0 | 2.0 | 0 | 0 | 0 | 1.5 | 9.2 | 89.3 |
| 2 | 1.8 | 0 | 0 | 0 | 1.3 | 7.9 | 90.8 |
| 4 | 1.2 | 0 | 0 | 0 | 1.0 | 7.0 | 92.0 |
| 6 | 1.0 | 0 | 0 | 0 | — | 5.0 | 95 |
| 8 | 0.8 | | | | | | |
| 10 | 0.5 | | | | | | |
| 12 | 0.8 | traces | 0 | 0 | 2.8 | 2.1 | 95.0 |
| 14 | 1.0 | 66.1 | 15.8 | 0 | 1.7 | 4.9 | 11.5 |
| 16 | 2.0 | 46.6 | 21.0 | 11.3 | 17.5 | 1.3 | 2.3 |
| 18 | 4 | 28.0 | 15.7 | 12.6 | 42.3 | 0.7 | 0.7 |
| 20 | 7 | 20.3 | 12.7 | 11.5 | 53.5 | 1.4 | 0.6 |
| 22 | 11 | 16.2 | 10.9 | 10.3 | 59.6 | 2.6 | 0.4 |
| 23'30" | 13 | 16.0 | 10.0 | 10.0 | 59.5 | 3.5 | 1.0 |

The detailed analysis of the results collected in this Table II show that:

during the 12 first minutes, the highly absorbed sorbitol whose average richness was greater than 85% was removed and, for certain fractions, than 90%; this explains the low true content of sorbitol of the previously analyzed maltitol fraction;

then from the minute 12 to the moment 18'30", the fraction extracted contained the major part of the higher hydrogenated limiting dextrins, of DP higher than or equal to 4 with a low content of hydrogenated products of DP 2 and DP 3, then from moment 18'30" to the moment 22'30", the maltotriitol enriched fraction was removed, with an average content of 57.3%, namely an equivalent of 71 liters/hour with 11% of dry matter.

The chromatographic fractionation installation was supplied as shown in Table III.

TABLE III

| | Maltitol rich hydrogenated hydrolyzate | Water | Total |
|---|---|---|---|
| Flow rate | 96.9 l/h | 393 l/h | 489.9 l/h |
| Density | 1.229 kg/l | | |
| Dry matter | 52.3% | | |
| Mass flow rate | 62.3 kg/h | | 62.3 kg/h |
| Richness in Maltitol | 73.1% | | |
| Mass flow rate of maltitol | 45.54 kg/h | | 45.54 kg/h |

In Table IV are collected the amounts and characteristics of the effluents withdrawn from the installation.

TABLE IV

| | Maltitol Fraction | Sorbitol fraction and combined dextrin fraction | Maltotriitol Fraction | Total |
|---|---|---|---|---|
| Flow rate | 152 l/h | 266 l/h | 71.9 l/h | 489.9 l/h |
| Density | 1.12 kg/l | 1.00 kg/l | 1.04 kg/l | |
| Dry matter | 28.5% | 2.4% | 10.0% | |
| Mass flow rate | 48.5 kg/h | 6.4 kg/h | 7.4 kg/h | |
| Richness in maltitol | 93.3% | 7% | 2% | |
| Mass flow rate of maltitol | 45.25 kg/h | 0.168 kg/h | 0.128 kg/h | 45.54 kg/h |

These results correspond to a maltitol extraction ratio of:

$$\frac{45.25}{45.54} = 99\%$$

and to an extraction yield of maltitol syrup of:

$$\frac{48.5}{62.3} = 77.8\%$$

This chromatographic fractionation installation thus operated for fourteen days. Tables V and VI below give the composition of the extracts as a function of time expressed in days.

TABLE V

| | (ENRICHED MALTITOL) | | | | | | |
|---|---|---|---|---|---|---|---|
| Days | 2 | 4 | 6 | 8 | 10 | 12 | 14 |
| DP ≧ 4 | 0.2 | 0.2 | 0.3 | 0.1 | 0.4 | 0.6 | 0.1 |
| DP 3 | 5.6 | 6.9 | 5.0 | 5.0 | 5.0 | 5.2 | 4.9 |
| Maltitol | 93.8 | 92.7 | 94.0 | 93.5 | 93.2 | 93.2 | 94.0 |
| Sorbitol | 0.4 | 0.2 | 0.7 | 1.4 | 1.4 | 1.0 | 1.0 |

TABLE VI

| | (ENRICHED MALTOTRIITOL) | | | | | | |
|---|---|---|---|---|---|---|---|
| Days | 2 | 4 | 6 | 8 | 10 | 12 | 14 |
| DP ≧ 4 | 40.5 | 44.8 | 44.6 | — | 36.1 | — | 37.4 |
| DP 3 | 57 | 51.9 | 53.4 | — | 59.5 | — | 59.6 |
| Maltitol | 2.1 | 2.9 | 1.4 | — | 3.4 | — | 2.6 |
| Sorbitol | 0.4 | 0.4 | 0.6 | — | 1.0 | — | 0.4 |

EXAMPLE 2—PROCESS ACCORDING TO THE INVENTION FOR THE PREPRATION OF A PRODUCT WITH HIGH MALTITOL CONTENT FROM A WHEAT STARCH

A wheat starch milk of dry matter content 37%, was liquefied at a pH of 6.3, at a temperature of 108° C. and with an addition of 0.3°/oo of liquefying enzyme of the type known under the trademark "THERMAMYL" of the NOVO Company. At the outlet of liquefaction installation, a thermal shock of 10 seconds at 130° C. was applied. The DE at the liquefaction outlet was less than 5.0.

The pH was adjusted at the outlet of the installation to a value of 5.5 and 0.55°/oo of β-amylase marketed under the name "SPEZYME BBA 1500" by the FINN-SUGAR Company, was added. The saccharification was carried out at this pH for 48 hours at 57° C.

At the end of saccharification, liquid chromatographic analysis showed the presence of:

| | | |
|---|---|---|
| Dextrose | 2.3% | by weight |
| Maltose | 61.3% | by weight |
| Trisaccharides | 7.5% | by weight |
| Products of DP 4 to DP 10 | 6.2% | by weight |
| Product of DP > 10 | 22.7% | by weight. |

After hydrogenation carried out as described in Example 1, followed by purification and concentration, a maltitol rich syrup was obtained whose composition was as follows:

| | | |
|---|---|---|
| Sorbitol | 3.3% | by weight |
| Maltitol | 60.4% | by weight |
| Trisaccharides | 10.2% | by weight |
| Products of DP 4 to DP 10 | 7.0% | by weight |
| Product of DP > 10 | 20.1% | by weight. |

Fractionation of this hydrolyzate rich in hydrogenated maltose followed in the chromatographic installation described in Example 1.

The installation was supplied in a manner which emerges from Table VII.

TABLE VII

| | Maltitol syrup | Water | Total |
|---|---|---|---|
| Flow rate | 90 l/h | 430 l/h | 520 l/h |
| Density | 1.25 kg/l | | |
| Dry matter | 51.5% | | |
| Mass flow rate | 56.3 kg/h | | 56.9 kg/h |
| Richness in maltitol | 60.4% | | |
| Mass flow rate of maltitol | 34 kg/h | | 34 kg/h |

The effluents extracted from the installation are identified in Table VIII.

TABLE VIII

| | Enriched maltitol | Sorbitol then hydrogenated limiting dextrins | Maltotriitol | Total |
|---|---|---|---|---|
| Flow rate | 145 l/h | 305 l/h | 70 l/h | 520 l/h |
| Density | 1.11 kg/l | 1.02 Kg/l | 1.03 kg/l | |
| Dry matter | 23% | 4.5% | 8.2% | |
| Mass flow rate | 37 kg/h | 14.0 kg/h | 5.9 kg/h | 56.9 kg/h |
| Richness in maltitol | 90.5% | 2% | 3.9% | |
| Mass flow rate of maltitol | 33.5 kg/h | 0.28 kg/h | 0.23 kg/h | 34.1 kg/h |

This result corresponds to an extraction ratio by weight of:

$$\frac{37}{56.3} = 67\% \text{ of maltitol syrup enriched to } 90.5\%$$

and of $$\frac{33.5}{34} = 98.5\% \text{ extraction of the maltitol}$$

Analysis of the enriched maltitol fraction gives the following results:

| | | |
|---|---|---|
| Sorbitol | 1.3% | by weight |
| Maltitol | 90.5% | by weight |
| DP 3 | 7.8% | by weight |
| DP 4 | 0.4% | by weight. |

Analysis of the enriched maltotriitol syrup fraction gives the following results:

| | | |
|---|---|---|
| Sorbitol | 0.4% | by weight |
| Maltitol | 3.9% | by weight |
| Maltotriitol | 51% | by weight |
| Maltotetraitol | 10.6% | by weight |
| Products of DP equal to 5 | 9.5% | by weight |
| Products of DP > 5 | 24.6% | by weight. |

It can be observed, from these different measurements that it was possible, by this fractionation process from a standard syrup obtained by saccharification with β-amylase alone and at the customary high concentration, to extract 98.5% of the maltitol with a richness of 90.5%.

This syrup is itself also characterized by the almost total absence of hydrogenated dextrins.

It was possible to extract conjointly a syrup enriched in maltotriitol with a richness of 51%.

In all cases (products coming from Examples 1 and 2), the effluents very highly enriched in maltitol were concentrated to dry matter contents most suitable for the various uses; these dry matter contents are generally from 65 to 90%.

The uses arising from the advantageous properties of the product obtained by the process according to the invention will be better understood by means of the following examples relating to advantageous embodiments, but not intended to limit the scope thereof.

EXAMPLE 3—APPLICATION OF THE PRODUCT OBTAINED ACCORDING TO THE INVENTION TO THE MANUFACTURE OF ANHYDROUS CRYSTALLINE MALTITOL

Recourse was had to a syrup obtained according to the invention characterized by the following composition, (the percentages are expressed on a dry basis):

| | | |
|---|---|---|
| Sorbitol | 1.1% | by weight |
| Maltitol | 92.4% | by weight |
| Maltotriitol | 6.1% | by weight |
| Products of DP ≧ 4 | 0.4% | by weight. |

This maltitol syrup was concentrated under reduced pressure to a 90% dry matter content at a temperature of 80° C.

This reduced mass was collected in a crystallizing vessel provided with a double jacket. After four hours of maintenance at 75° C., a start of very regular crystallization is seen to appear (spontaneous nucleation).

Cooling of the crystallizing vessel then follows at a speed of 1° C./hour from 75° C. to 25° C. in 50 hours.

The crystalline mass is drained on a centrifugical draining device.

The draining of the mother-liquors is very easy, the clarification (washing) of the crystals is carried out with cold distilled water.

After this operation the crystals are collected and dried on a fluidized bed drying unit to a water content less than 0.5%.

The crystalline maltitol was obtained with a yield of 63% (with respect to dry matter subjected to crystallization) and showed a chemical purity of 99.2% by high pressure liquid chromatography.

Its rotatory power (aqueous 10% solution) at 20° C., sodium D line is +106° C.

Its content of reducing sugars was less than 0.01%.

Its melting temperature at the peak, read on a D.S.C. SETARAM 111 differential thermal analysis apparatus with 50 mg of substance, heating speed of 2° C./min. was 150.7° C.

It is non hydroscopic and appears as a free-flowing powder.

EXAMPLE 4—APPLICATION OF THE PRODUCT OBTAINED ACCORDING TO THE INVENTION TO THE MANUFACTURE OF BOILED CANDY

Recourse was had to a syrup obtained according to the invention characterized by the following composition (the percentages are expressed on a dry basis):

| Sorbitol | 3.4% by weight |
|---|---|
| Maltitol | 89.2% by weight |
| Maltotriitol | 6.9% by weight |
| Products of DP ≧ 4 | 0.5% by weight. |

A quantity of 350 g of this syrup, with 75% dry matter, is heated in a copper vessel on an electric plate to a temperature of 180° C. with frequent stirring.

The boiled syrup mass was allowed to cool to a temperature of 130°-140° C.

The usual acid, aroma and colouring are carefully incorporated before running the boiled mass onto cold marble.

The acid used is citric acid.

The flavoring was lemon.

The mass cooled to 60°-80° C. is cut up into bonbons of 15×15 mm.

The bonbons are wrapped by means of waterproof paper.

They are bright and show a high sweetened flavour as well as a sweet taste identical with that of saccharose.

The final moisture content of the boiled candy is in the vicinity of 1%.

The composition in dry matter of the finished product is as follows:

| Maltitol syrup | 97.8% by weight |
|---|---|
| Citric acid | 1% by weight |
| Lemon flavouring | 0.2% by weight |
| Colouring | sufficient amount |
| Water | 1% by weight. |

EXAMPLE 5—APPLICATION OF THE PRODUCT OBTAINED ACCORDING TO THE INVENTION TO THE MANUFACTURE OF A BEVERAGE

Recourse was had to a syrup obtained according to the invention characterized by the following composition (the percentages are expressed on a dry basis):

| Sorbitol | 2.9% by weight |
|---|---|
| Maltitol | 91.6% by weight |
| Maltotriitol | 5.3% by weight |
| Products of DP ≧ 4 | 0.2% by weight. |

The composition provided for the beverage was as follows:

| Maltitol syrup with 75% dry matter | 170 g |
|---|---|
| Citric acid | 2.6 g |
| Lemon flavor paste | 1.4 g |
| Water | additional amount to make 1 liter. |

To prepare this beverage, the maltitol syrup is mixed with 300 ml of water. To this mixture is added the flavoring and the acid and then the rest of the water.

The beverage is then carbonated by the direct injection of carbon dioxide into the vessel.

The finished beverage shows a refractive index of 1.3525. Its sweetness level is equivalent to that of a beverage with saccharose, the impression left in the mouth is, moreover, very pleasant and the flavoring is more perceptible and more durable than that of the same beverage prepared with 100 g/liter of saccharose.

EXAMPLE 6—APPLICATION OF THE PRODUCT OBTAINED ACCORDING TO THE INVENTION TO THE MANUFACTURE OF CHEWING GUM

Recourse was had to a product obtained according to the invention characterized by the following composition (the percentages are expressed on a dry basis):

| Sorbitol | 0.7% by weight |
|---|---|
| Maltitol | 94.8% by weight |
| Maltotriitol | 4.4% by weight |
| Products of DP ≧ 4 | 0.1% by weight. |

The syrup is concentrated to 91% of dry matter and is run into polyethylene basins.

After 24 hours of cooling to 20° C., the white loaves of 3 centimeters thickness were demolded and broken up. The fragments obtained were ground and the powder was dried in a fluidized bed drying unit. It was then sifted to provide a powder flowing freely and corresponding to the following granulometric analysis:

0% of retention on a sieve of 315 microns
30% of particles of dimensions comprised between 315 and 250 microns
35% of particles with dimensions comprised between 250 and 160 microns
25% of particles of dimensions comprised between 160 and 71 microns
10% of particles less than 71 microns.

By means of this powder a chewing gum of the following formula was manufactured:

| gum base 34/42 | 25% by weight |
|---|---|
| hydrogenated glucose syrup of the brand LYCASIN 80/55 | 20% by weight |
| powdered maltitol according to the preceding analyses | 55% by weight |

| flavoring | 1.2% by weight |
| coloring | sufficient amount |

For the manufacture, the gum base was softened by bringing it to a temperature of about 70°–80° C. and it was placed in a kneading trough preheated to 45°–50° C.

Hydrogenated glucose syrup of the trademark LYCASIN 80/55 preheated to 45° C. was added thereto and it was kneaded for two minutes.

The third of the maltitol powder obtained as previously described was then added and it was again kneaded for two minutes following which a further third of the maltitol powder was introduced.

After two minutes of kneading, the remainder of the maltitol powder was added, then the flavoring and the coloring.

It was kneaded again for two minutes, then rolled and the dough cut up.

Submitted to a specialized taste panel, the product was judged superior to "sugarless" chewing gums customarily found on the market. The chewing gum thus obtained is tender, elastic, non-sticky. The sweet taste is very pleasant.

I claim:

1. In a process for the preparation of a syrup rich in maltitol proper to provide crystalline maltitol comprising the steps of
   liquefying a starch milk,
   subjecting the liquefied starch milk to the action of a saccharifying enzyme to provide a maltose syrup,
   catalytically hydrogenating said maltose syrup with Ruthenium or Raney nickel catalysts to provide a maltitol syrup, the improvement comprising
   selecting for liquefying a starch milk having a dry matter content of 25 to 45% by weight and liquefying said starch milk to a DE from higher than 2 to about 25,
   subjecting the liquefied starch milk to saccharification under the action of a saccharifying enzyme from the group consisting of $\beta$-amylases of vegetal or bacterial origin until a maltose syrup having a maltose content of as low as from 50 to 80% by weight is obtained,
   catalytically hydrogenating said maltose syrup to provide a maltitol syrup also containing sorbitol, maltotriitol and polyols of degree of polymerization $\geq 4$,
   subjecting said maltitol syrup to a chromatographic fractionation providing a fraction rich in sorbitol, a fraction rich in polyols of degree of polymerization $\geq 4$, a fraction rich in maltotriitol and a fraction rich in maltitol comprising, the percentages being expressed by weight based on the dry matter content
   at least 87% of maltitol,
   less than 1% of polyols of a degree of polymerization $\geq 4$,
   less than 5% of sorbitol,
   a proportion of maltotriitol comprised between 2.5 and 13%, and
   collecting said fraction rich in maltitol.

* * * * *